(12) United States Patent
Sakai et al.

(10) Patent No.: US 12,158,366 B2
(45) Date of Patent: Dec. 3, 2024

(54) LIQUID SURFACE DETECTION DEVICE, ATOMIZATION DEVICE, AND CULTURE DEVICE

(71) Applicant: PHC Holdings Corporation, Tokyo (JP)

(72) Inventors: Yuta Sakai, Saitama (JP); Masaki Yoshida, Gunma (JP); Kousuke Honda, Ehime (JP); Akito Sawai, Mie (JP); Megumi Onda, Tokyo (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 352 days.

(21) Appl. No.: 17/724,109

(22) Filed: Apr. 19, 2022

(65) Prior Publication Data
US 2022/0252445 A1    Aug. 11, 2022

Related U.S. Application Data

(63) Continuation of application No. PCT/JP2020/038226, filed on Oct. 9, 2020.

(30) Foreign Application Priority Data

Oct. 30, 2019 (JP) .................................. 2019-197497

(51) Int. Cl.
*G01F 23/30* (2006.01)
*B05B 17/06* (2006.01)
*C12M 3/00* (2006.01)

(52) U.S. Cl.
CPC .......... *G01F 23/30* (2013.01); *B05B 17/0607* (2013.01); *C12M 3/00* (2013.01)

(58) Field of Classification Search
None
See application file for complete search history.

(56) References Cited

U.S. PATENT DOCUMENTS

2009/0000317 A1\* 1/2009 Schill ........................ F25C 1/00
239/338

FOREIGN PATENT DOCUMENTS

| DE | 19608866 A1 | 9/1997 |
|----|----|----|
| JP | H07-063596 A | 3/1995 |
| JP | H10-262896 A | 10/1998 |
| JP | 3883654 B2 \* | 2/2007 |
| JP | 2008-036394 A | 2/2008 |
| JP | 2010-249337 A | 11/2010 |
| JP | 2011-036771 A | 2/2011 |

(Continued)

OTHER PUBLICATIONS

International Search Report dated Dec. 28, 2020 issued in International Patent Application No. PCT/JP2020/038226, with English translation.

(Continued)

*Primary Examiner* — Daniel S Larkin
(74) *Attorney, Agent, or Firm* — Rimon P.C.

(57) ABSTRACT

This liquid surface detection device comprises: a liquid retention part in which hydrogen peroxide water is retained, the hydrogen peroxide water to be atomized by a vibrating plate in which a through-hole is provided; a float positioned inside the liquid retention part; and a sensor that detects, via the float, the arrival of the liquid surface of the hydrogen peroxide water retained in the liquid retention device at a prescribed position.

17 Claims, 7 Drawing Sheets

(56) References Cited

FOREIGN PATENT DOCUMENTS

| JP | 2011-136035 A | 7/2011 |
|---|---|---|
| JP | 2012-087968 A | 5/2012 |

OTHER PUBLICATIONS

Extended European Search Report dated Oct. 21, 2022 issued in the corresponding European Patent Application No. 20881080.4.

* cited by examiner

LIQUID SURFACE DETECTION DEVICE, ATOMIZATION DEVICE, AND CULTURE DEVICE

CROSS-REFERENCE OF RELATED APPLICATIONS

This application is a continuation of International Patent Application No. PCT/JP2020/038226, filed on Oct. 9, 2020, the disclosure of which is incorporated herein by reference in its entirety. International Patent Application No. PCT/JP2020/038226 is entitled to (or claims) the benefit of Japanese Patent Application No. 2019-197497, filed on Oct. 30, 2019, the disclosure of which is incorporated herein by reference in its entirety.

TECHNICAL FIELD

The present disclosure relates to a liquid level detection device, an atomization device, and a culture device.

BACKGROUND ART

In the related art, a decontamination device that atomizes decontamination liquid and releases it into a culture device is known as a device for decontaminating the inside of a culture device for culturing objects such as cells and microorganisms.

As a decontamination device, for example, PTL 1 discloses an ultrasonic atomizer that atomizes the decontamination liquid at the liquid level of the decontamination liquid by vibrating a piezoelectric element with ultrasonic waves.

CITATION LIST

Patent Literature

PTL 1
Japanese Patent Application Laid-Open No. 2011-36771

SUMMARY OF INVENTION

Technical Problem

If the liquid level position in the decontamination device can be known, the decontamination device can be operated properly. However, it is difficult to accurately detect the liquid level of the decontamination liquid contained inside the ultrasonic atomizer disclosed in PTL 1.

An object of the present disclosure is to provide a liquid level detection device that can correctly detect the liquid level of the decontamination liquid inside a decontamination device, an atomization device including the liquid level detection device, and a culture device including the atomization device.

Solution to Problem

A liquid level detection device according to the present disclosure includes: a liquid reservoir configured to store hydrogen peroxide solution to be atomized by a diaphragm including a through hole; a float disposed in the liquid reservoir; and a sensor configured to detect a fact that a liquid level of the hydrogen peroxide solution stored in the liquid reservoir has reached a predetermined position, by using the float.

An atomization device according to the present disclosure includes: the above-described liquid level detection device; and the above-described diaphragm.

A culture device according to the present disclosure includes the above-described atomization device.

Advantageous Effects of Invention

According to the present disclosure, it is possible to provide a liquid level detection device that can correctly detect the liquid level of the decontamination liquid inside a decontamination device, an atomization device including the liquid level detection device, and a culture device including the atomization device.

BRIEF DESCRIPTION OF DRAWINGS

FIG. 2 is a perspective view illustrating an example of an external appearance of an atomization device according the embodiment of the present disclosure the;

DESCRIPTION OF EMBODIMENTS

An embodiment the present disclosure is described in detail below with reference to the accompanying drawings. Note that the embodiment described below is an example, and the present disclosure is not limited to the embodiment.

Figure 1:
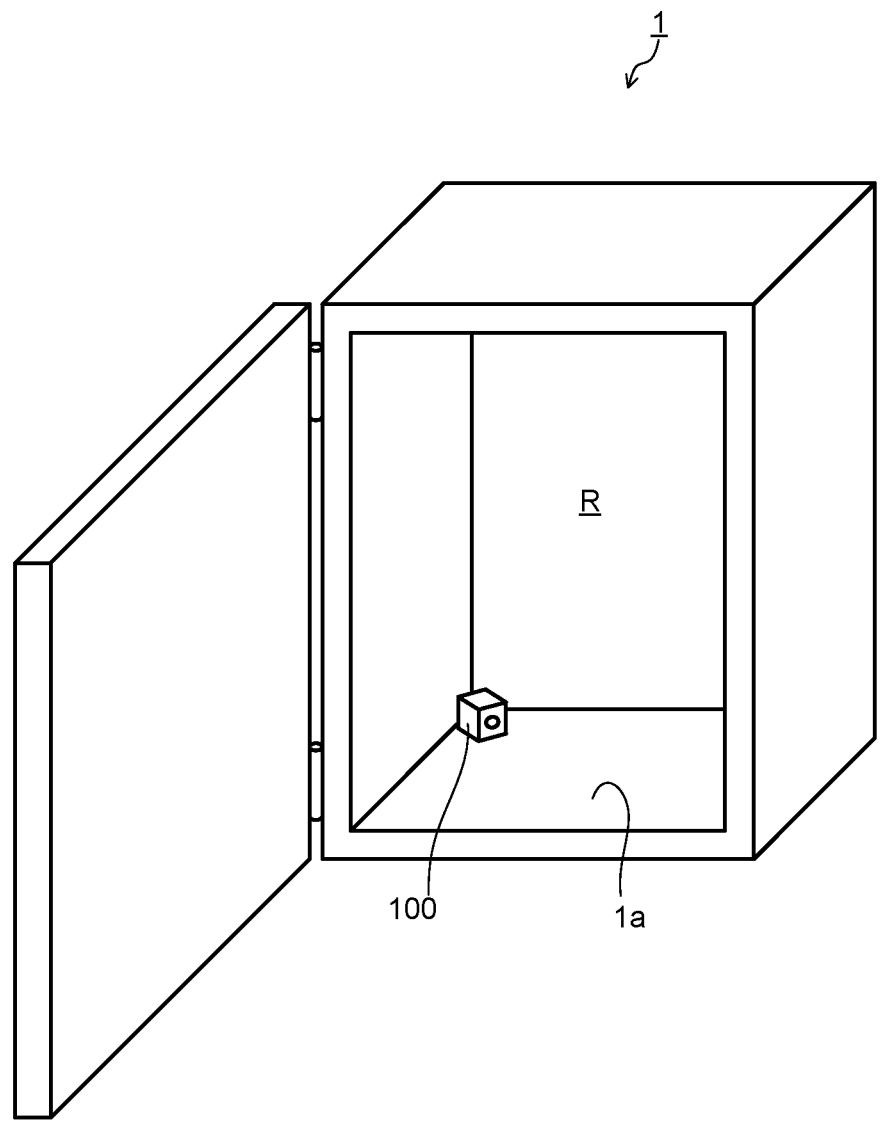
FIG. 1 is a schematic view illustrating an example of a culture device according to an embodiment of the present disclosure.

FIG. 1 is a schematic view illustrating an example of culture device 1 according to the present disclosure.

In culture chamber R as its internal space, culture device 1 can perform growing of plants, culture of plants cells, tissues, and organs, breeding and growing of insects and the like. In the following description, the object of culture, breeding and growing the like by the culture device 1 is simply referred to as object.

When culture device 1 performs culture, breeding, growing and the like of the above-described object, culture chamber R must be kept clean. Culture device 1 performs decontamination operation of culture chamber R by performing a predetermined operation.

Atomization device 100 is a decontamination device that is disposed in culture chamber R when culture device 1 performs the decontamination operation. Note that 1a in FIG. 1 represents a surface (i.e., installation surface) where atomization device 100 is disposed. Atomization device 100 stores in its inside decontamination liquid used for the decontamination operation, and in the decontaminate operation of culture device 1, atomization device 100 emits the decontamination liquid to culture chamber R in a mist form by atomizing the decontamination liquid. Note that atomization device 100 may be provided to culture device 1.

Figure 2:
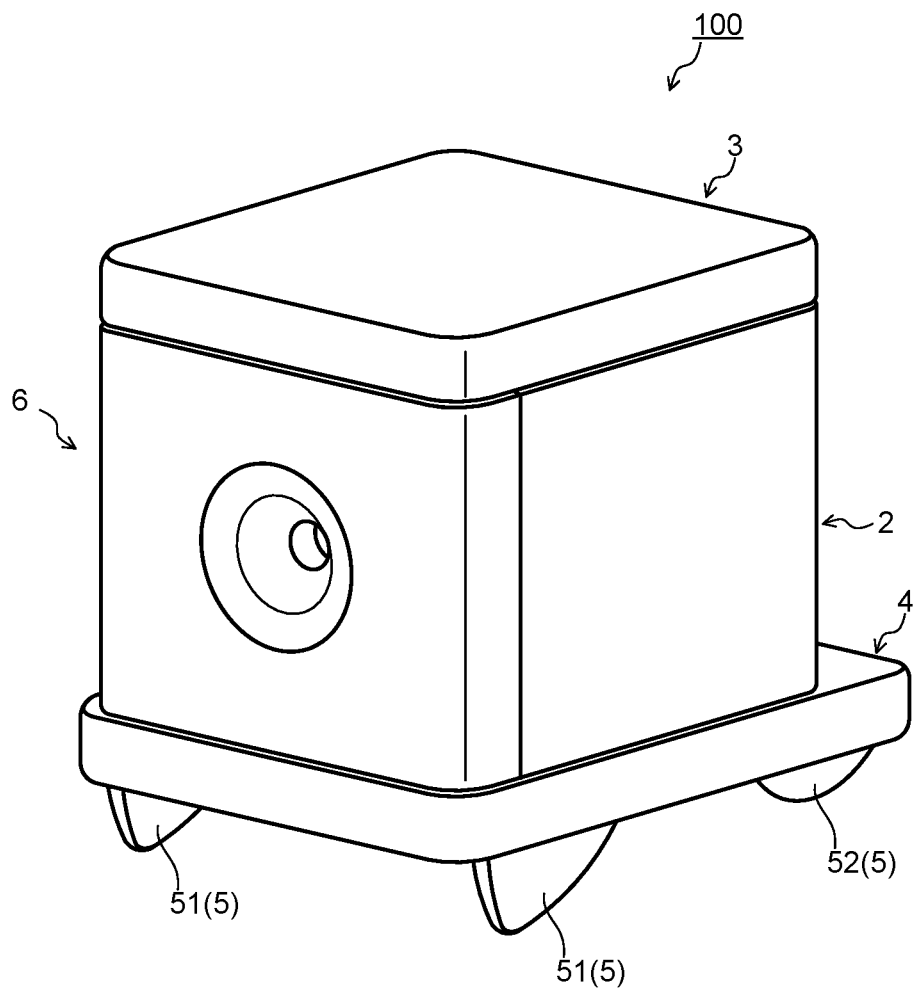
Figure 3:
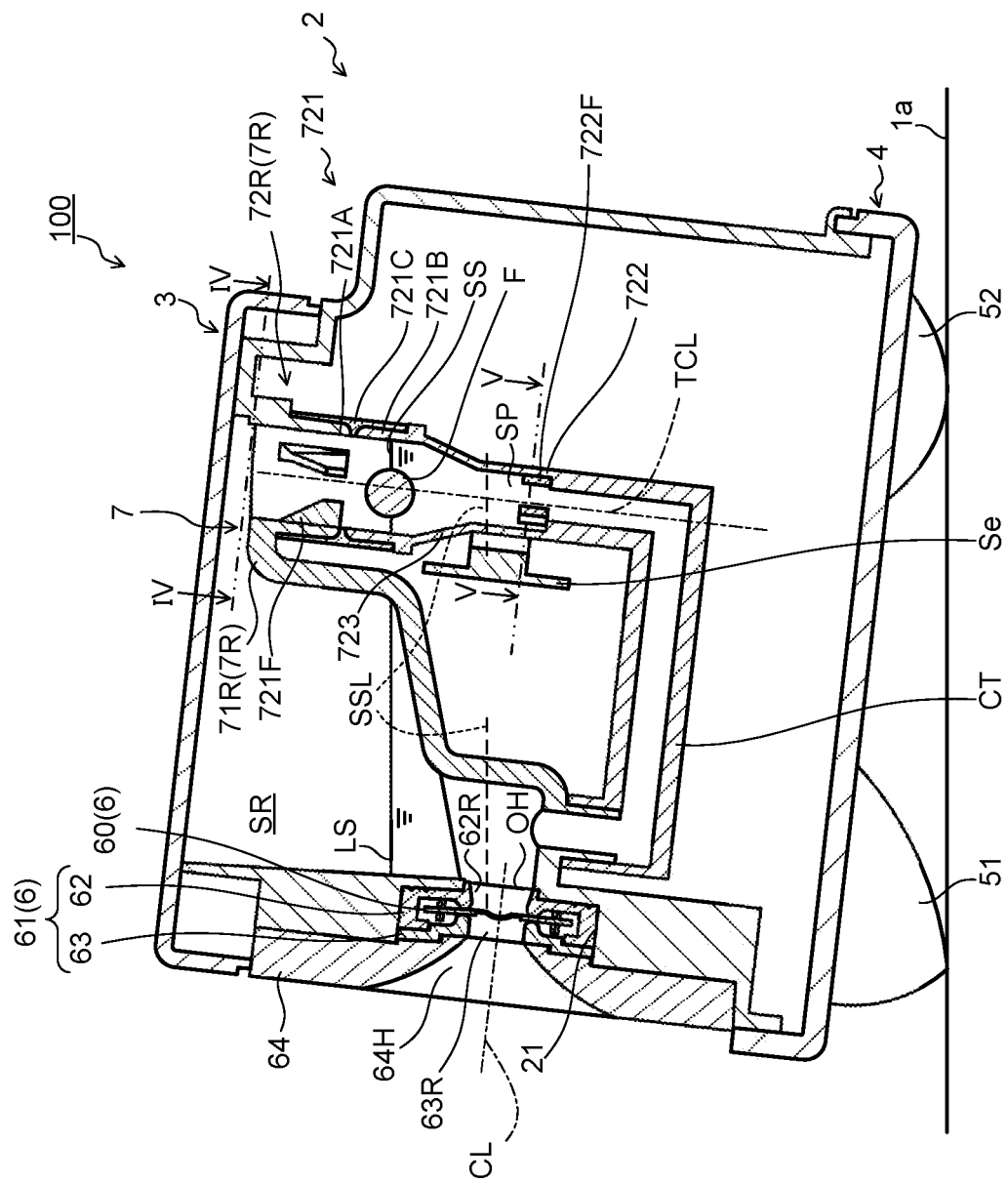
FIG. 3 is a longitudinal sectional view of the atomization device including a liquid level detection device according the embodiment of the present disclosure, taken along a vertical plane.
Figure 4:
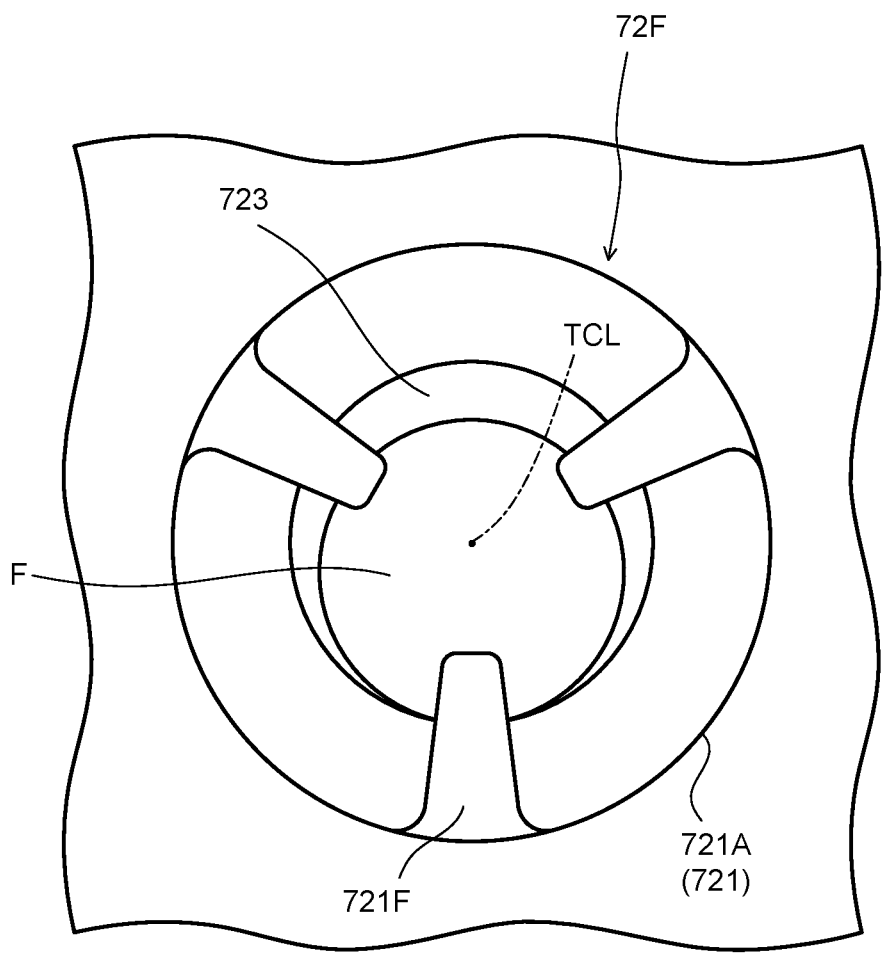
FIG. 4 is a diagram taken along IV-IV in FIG. 3.
Figure 5:
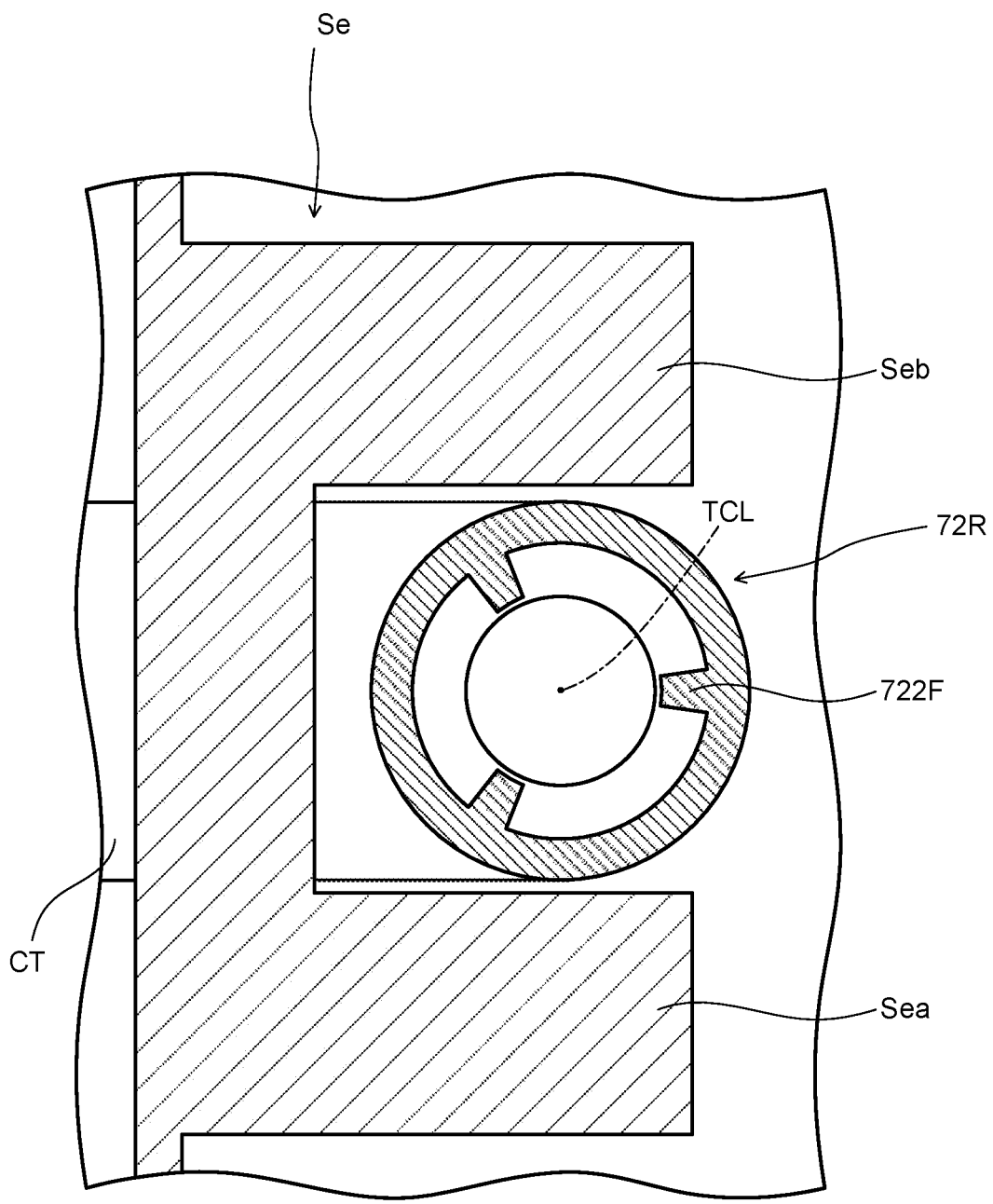
FIG. 5 is a sectional view taken along line V-V of FIG. 3.

Next, atomization device 100 provided in liquid level detection device 7 of the present embodiment is described, with reference to FIGS. 2 to 5. FIG. 2 is a perspective view illustrating an example of an external appearance of atomization device 100. FIG. 3 is a longitudinal sectional view illustrating atomization device 100 including liquid level detection device 7, taken along a vertical plane. FIG. 4 is a diagram taken along IV-IV in FIG. 3. FIG. 5 is a sectional view taken along line V-V of FIG. 3. The following description assumes that the decontamination liquid used for the decontamination operation of culture device 1 is hydrogen peroxide solution.

Atomization device 100 includes main body part 2, lid 3, supporting member 4, leg 5 and atomization mechanism 6.

Main body part 2 includes liquid supplying reservoir 71R described later, and hydrogen peroxide solution is stored in storage space SR (see FIG. 3), which is a space surrounded by liquid supplying reservoir 71R.

Depression 21 is formed in the front outer surface of main body part 2. Atomization mechanism 6 is disposed in depression 21. Outlet OH is formed in main body part 2. Outlet OH is a through hole that is open at the bottom surface of depression 21, and is a passage hole through which the hydrogen peroxide solution that flows out of storage space SR passes.

Lid 3 is a member that covers main body part 2 from the upper side. Supporting member 4 is a member attached on the lower side of main body part 2 and supports main body part 2.

Legs 5 are provided at the bottom surface of supporting member 4. Legs 5 include a pair of front legs 51 on the front side, and a pair of rear legs 52 on the rear side. The size of each of front legs 51 in the vertical direction is greater than the size of each of rear legs 52 in the vertical direction. In this manner, atomization device 100 is disposed such that with respect to installation surface 1a, an end portion of supporting member 4 on the front leg 51 side is located on the upper side than an end portion of supporting member 4 on the rear leg 52 side. The inclination angle of supporting member 4 with respect to installation surface 1a is, for example, six degrees.

In addition, as viewed from the lateral side of atomization device 100, the lower side outline of front legs 51 includes a pointed portion and a curved portion, and front legs 51 are in substantially point contact with installation surface 1a. In addition, when atomization device 100 is viewed from the side surface, the outline of rear legs 52 on the installation surface 1a side is curved, and rear legs 52 are in substantially point contact with installation surface 1a.

In this manner, the contact area between front legs 51 and installation surface 1a, and the contact area between rear legs 52 and installation surface 1a can be reduced as much as possible, and thus the hydrogen peroxide solution atomized by atomization device 100 can be diffused over a wide range of the region on the lower side of supporting member 4 in installation surface 1a.

Next, atomization mechanism 6 is described with reference to FIG. 3.

Atomization mechanism 6 includes diaphragm 60, holding member 61, and nozzle 64.

Diaphragm 60 has a circular plate shape. The center portion of diaphragm 60 has a substantially dome shape protruding to the front side. A plurality of through holes through which hydrogen peroxide solution passes is formed at a center portion of diaphragm 60. Note that through holes are so small that they are not visible to the naked eye. The center portion of diaphragm 60 vibrates back and forth under the vibration of the outer periphery portion of diaphragm 60. When diaphragm 60 vibrates, the hydrogen peroxide solution is passed through the through holes and emitted in the form of minute droplets. That is, when diaphragm 60 vibrates, the hydrogen peroxide solution is atomized. The center portion of diaphragm 60 is made of metal, and is for example, made of nickel. Note that diaphragm 60 is disposed by holding member 61 such that the outer surface of diaphragm 60 faces the obliquely upper side. The inclination angle between central axis CL of diaphragm 60 and the horizontal surface is, for example, six degrees.

The outer periphery portion of diaphragm 60 is made of piezoelectric ceramic. The outer periphery portion of diaphragm 60 vibrates back and forth by the piezoelectric effect when an AC voltage is applied from a power source (not illustrated in the drawing) provided in atomization device 100, through an electrode.

Holding member 61 sandwiches the outer periphery portion of diaphragm 60 from the inner surface side and the outer surface side of diaphragm 60. Holding member 61 is composed of inner holding member 62 and outer holding member 63. Note that both inner holding member 62 and outer holding member 63 are made of silicon.

Inner holding member 62 supports the outer periphery portion of diaphragm 60 from the inner surface side. Supply path 62R communicating with outlet OH is formed in inner holding member 62, and the hydrogen peroxide solution in storage space SR is guided to diaphragm 60 through outlet OH and supply path 62R.

Outer holding member 63 supports the outer periphery portion of diaphragm 60 from the outer surface side. Jetting path 63R is formed in outer holding member 63, and the hydrogen peroxide solution atomized by diaphragm 60 passes through jetting path 63R.

Nozzle 64 is a member in which a jetting hole 64H, through which the hydrogen peroxide solution past minute through holes formed in diaphragm 60 in a mist form passes, is formed.

Next, liquid level detection device 7 is described with reference to FIGS. 3 to 5. Liquid level detection device 7 of the present embodiment is formed as a part of atomization device 100. Note that liquid level detection device 7 may be separable from atomization device 100.

As illustrated in FIG. 3, liquid level detection device 7 includes liquid reservoir 7R, float F, connection tube CT, and sensor Se.

Liquid reservoir 7R includes liquid supplying reservoir 71R and detecting reservoir 72R. The hydrogen peroxide solution atomized by diaphragm 60 is stored in liquid supplying reservoir 71R.

Detecting reservoir 72R includes upper cylindrical part 721, lower cylindrical part 722 and tapered cylindrical part 723. Lower cylindrical part 722 and tapered cylindrical part 723 are formed of a transparent material. Note that as long as at least lower cylindrical part 722 is formed of a transparent material, other portions need not necessarily be formed of a transparent material. In FIG. 3, TCL represents the central axis of detecting reservoir 72R.

Upper cylindrical part 721 is a cylindrical portion located on the upper side than lower cylindrical part 722 and tapered cylindrical part 723. Upper cylindrical part 721 is composed of upper portion 721A, lower portion 721B, and connecting portion 721C. Upper portion 721A is a topmost portion of upper cylindrical part 721, and is composed of the same material as liquid supplying reservoir 71R. Three upper protrusion pieces 721F protruding from the inner peripheral surface of upper portion 721A toward central axis TCL of detecting reservoir 72R are formed at the inner peripheral surface of upper portion 721A (see FIG. 4). Upper protrusion piece 721F has a substantially plate shape. Lower portion 721B is a lowermost portion of upper cylindrical part 721, and is formed integrally with tapered cylindrical part 723 and lower cylindrical part 722. Connecting portion 721C is, for example, a silicon tube, and connects between upper portion 721A and lower portion 721B.

Lower cylindrical part 722 is located on the lower side than upper cylindrical part 721. Detection space SP where float F can be contained inside is formed on the upper side of lower cylindrical part 722. The inner diameter of lower cylindrical part 722 is smaller than the inner diameter of the upper cylindrical part, and greater than the outer diameter of float F. As illustrated in FIG. 5, three lower protrusion pieces 722F protruding from the inner peripheral surface of detecting reservoir 72R toward central axis TCL of detecting reservoir 72R are formed at the inner peripheral surface of detecting reservoir 72R. Note that lower protrusion piece 722F has a substantially plate shape.

Tapered cylindrical part 723 is located between upper cylindrical part 721 and lower cylindrical part 722, and is connected to lower portion 721B and lower cylindrical part 722. The inner diameter of tapered cylindrical part 723 decreases as the distance to lower cylindrical part 722 decreases. The inner diameter at the upper end of tapered cylindrical part 723 is the same as the inner diameter of upper cylindrical part 721, and the inner diameter at the lower end of tapered cylindrical part 723 is the same as the inner diameter of lower cylindrical part 722.

Float F is disposed in detecting reservoir 72R, and floated on the hydrogen peroxide solution in detecting reservoir 72R. Thus, the height of liquid level SS and the height of float F have a relationship in which one of them is determined when the other is determined. Float F is composed of an opaque material. In addition, float F has a spherical shape.

The upward movement of float F is limited by upper protrusion pieces 721F, and the downward movement of float F is limited by lower protrusion pieces 722F. That is, the movable range of float F in detecting reservoir 72R is the range between upper protrusion pieces 721F and lower protrusion pieces 722F.

Connection tube CT has a bent shape. Connection tube CT is located on the lower side of liquid supplying reservoir 71R and detecting reservoir 72R. One end of connection tube CT is connected to liquid supplying reservoir 71R from the lower side, and the other end of connection tube CT is connected to detecting reservoir 72R from the lower side. In this manner, liquid supplying reservoir 71R is connected to detecting reservoir 72R through connection tube CT, and liquid level LS of the hydrogen peroxide solution in liquid supplying reservoir 71R and liquid level SS of the hydrogen peroxide solution in detecting reservoir 72R are at the same height.

Sensor Se is, for example, an optoelectronic sensor such as a photo-microsensor, and detects the fact that liquid level LS of the hydrogen peroxide solution stored in liquid supplying reservoir 71R has reached a predetermined position, by using float F.

In the present embodiment, the predetermined position is set at the position of sensor detection line SSL illustrated in FIG. 3. Sensor detection line SSL represents the same height as the upper end of the center portion where the through hole is formed in diaphragm 60. Note that the predetermined position is located on the upper side than at least connection tube CT.

As illustrated in FIG. 5, sensor Se is located at a position lower than upper cylindrical part 721 in a vertical direction to surround the periphery of lower cylindrical part 722. Sensor Se includes light emission part Sea and light reception part Seb. Light emission part Sea emits detecting light toward light reception part Seb. The detecting light emitted by light emission part Sea passes through detection space SP of lower cylindrical part 722 and goes toward light reception part Seb. Light reception part Seb receives the detecting light. Sensor Se outputs a detection signal when light reception part Seb stops receiving the detecting light. In the present embodiment, the light from light emission part Sea is blocked when float F is housed in detection space SP. That is, when light reception part Seb stops detecting the detecting light from light emission part Sea, the position of float F is detected, and the position of liquid level SS is detected based on the detected position of float F. Since liquid level SS and liquid level LS are at the same height, liquid level detection device 7 practically detects liquid level LS by detecting liquid level SS.

In other words, the size of each portion of liquid supplying reservoir 71R and detecting reservoir 72R, the positions of sensor Se and diaphragm 60, and the sizes of front legs 51 and rear legs 52 in the vertical direction are adjusted such that the detecting light from light emission part Sea is blocked by float F when liquid level LS reaches the predetermined position Next, operations of liquid level detection device 7, atomization device 100, and culture device 1 during a decontamination operation are described.

First, the user detaches lid 3 from main body part 2, fills storage space SR of atomization device 100 with the hydrogen peroxide solution, and attaches lid 3 to the upper part of main body part 2 to cover it. Next, the user disposes atomization device 100 at installation surface 1a by opening the door of culture device 1, and the user electrically connects atomization device 100 to culture device 1. When culture device 1 and atomization device 100 are connect to each other, culture device 1 can control atomization device 100.

Next, when the user turns on the power source of culture device 1 and performs a predetermined operation at an operation panel (not illustrated in the drawing) of culture device 1, culture device 1 turns on the power source of atomization device 100. When the power source of atomization device 100 applies an AC voltage to diaphragm 60, diaphragm 60 vibrates back and forth at a predetermined frequency. When diaphragm 60 vibrates, the hydrogen peroxide solution in contact with the inner surface of diaphragm 60 passes through the through hole. When the hydrogen peroxide solution passes through the through hole, minute droplets are formed and emitted (i.e., atomized) to culture chamber R.

The hydrogen peroxide emitted to culture chamber R is sent to every corner of culture chamber R by an air blaster (not illustrated in the drawing) of culture device 1. The hydrogen peroxide emitted to culture chamber R is decomposed into a hydroxyl radical and a hydroxide ion. When the hydroxyl radical causes a chain reaction of taking electrons from contaminants in culture chamber R, the contaminants in culture chamber R are removed.

As the hydrogen peroxide solution in liquid supplying reservoir 71R is atomized, liquid level LS and liquid level SS are lowered. In addition, along with the lowering of liquid level SS, float F is also lowered.

When a predetermined time elapses after the power source of atomization device 100 is turned on, culture device 1 stops the operation of the power source of atomization device 100. In this manner, the vibration of diaphragm 60 stops.

In the case where liquid level LS reaches a predetermined position such as sensor detection line SSL before the predetermined time elapses, culture device 1 stops the atomizing of the hydrogen peroxide solution at atomization device 100.

When liquid level LS, i.e., liquid level SS, reaches sensor detection line SSL, the detecting light from light emission part Sea is blocked by float F, and light reception part Seb stops receiving the detecting light. When light reception part Seb stops receiving the detecting light, sensor Se outputs a detection signal to culture device 1. When the detection signal from sensor Se is input, culture device 1 stops the operation of the power source of atomization device 100 to stop the vibration of diaphragm 60.

When diaphragm 60 stops the vibration, at least all through holes of diaphragm 60 are immersed in the hydrogen peroxide solution.

Figure 6:
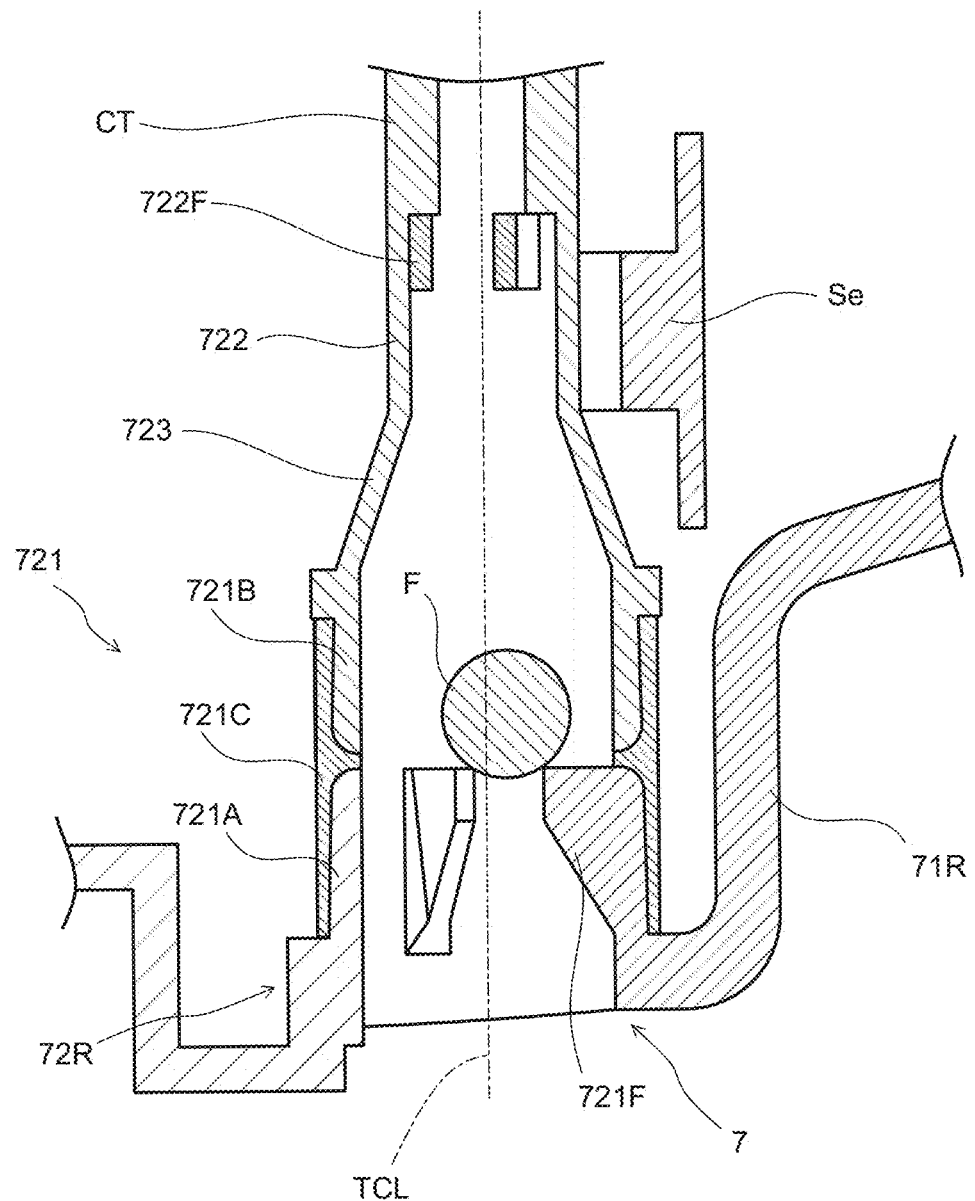
FIG. 6 is a longitudinal sectional view illustrating a part of the liquid level detection device according the embodiment of the present disclosure, and a state where the liquid level detection device is disposed upside down.
Figure 7:
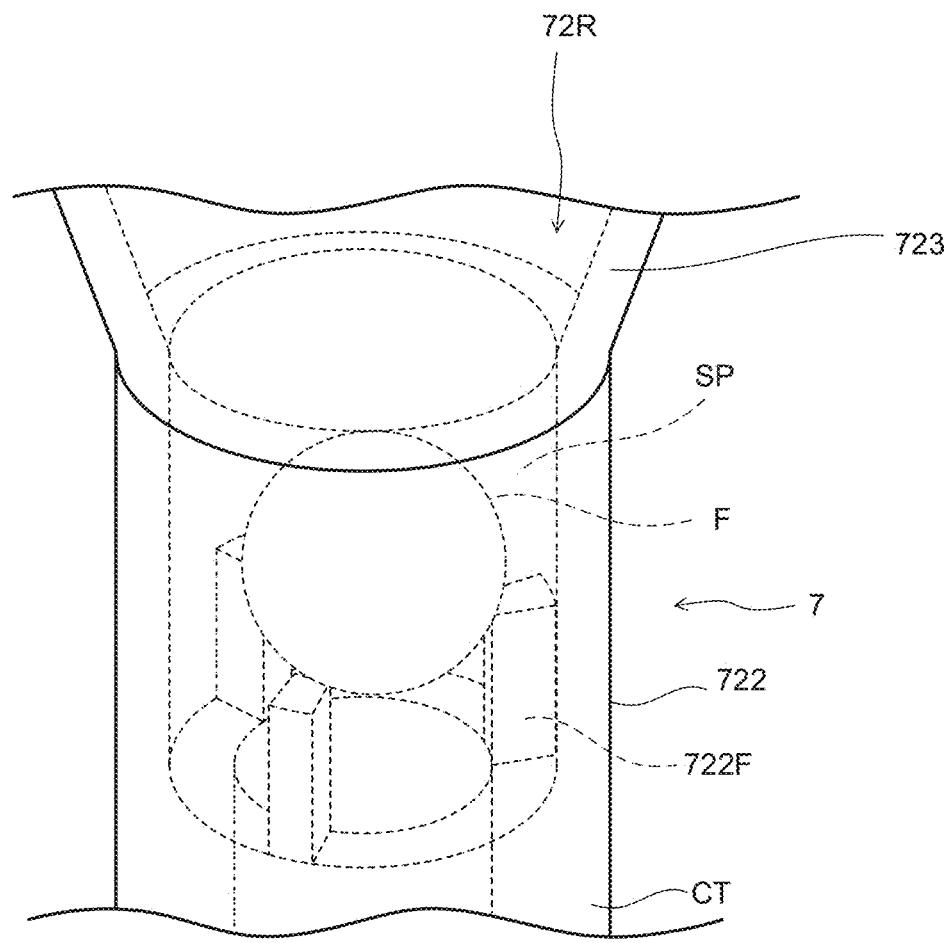
FIG. 7 is a diagram illustrating a state where a float provided in the liquid level detection device according the embodiment of the present disclosure is placed at a lower protrusion piece.

Note that after the decontamination operation of culture chamber R is completed, the hydrogen peroxide solution remaining inside atomization device 100 is discarded by the user. A function of liquid level detection device 7 during the discard of the remaining hydrogen peroxide solution is described below with reference to FIGS. 6 and 7. FIG. 6 is a longitudinal sectional view illustrating a part of the liquid level detection device as shown in FIG. 3 (a part around upper cylindrical part 721). Note that the liquid level detection device in FIG. 6 is disposed upside down, with central axis TCL of the detecting reservoir being perpendicular to the horizontal surface. FIG. 7 is a diagram illustrating a state where float F provided in the liquid level detection device as shown in FIG. 3 is placed at lower protrusion pieces 722F. In FIG. 7, lower cylindrical part 722, tapered cylindrical part 723, parts inside connection tube CT and float Fare illustrated with the broken lines.

When the decontamination of culture chamber R is completed, the user takes out atomization device 100 from culture chamber R, detaches lid 3 from main body part 2 of atomization device 100, and tilts atomization device 100. When atomization device 100 is tilted, the hydrogen peroxide solution in liquid supplying reservoir 71R, detecting reservoir 72R and connection tube CT flows to the outside of main body part 2.

Here, when the user changes the orientation of atomization device 100 upside down, liquid level detection device 7 is brought into a state where float F is placed at the bottom surface of upper protrusion pieces 721F as illustrated in FIG. 6. Since twice the distance from the central axis TCL side end of upper protrusion pieces 721F to central axis TCL is smaller than the outer diameter of float F, float F does not move to the upper side (in FIG. 6, the lower side) than the bottom surface of upper protrusion pieces 721F. That is, when float F is located on the uppermost side, float F is in contact with the bottom surface of upper protrusion pieces 721F (see FIG. 6), and float F does not fit to the upper end portion of detecting reservoir 72R, i.e., a portion between upper protrusion pieces 721F.

When the discard of the hydrogen peroxide solution in liquid reservoir 7R is completed, the user changes the orientation of atomization device 100 disposed upside down to the orientation illustrated in FIG. 3. At this time, as illustrated in FIG. 7, liquid level detection device 7 is set to a state where float F is placed at the top surface of lower protrusion pieces 722F. Since twice the distance from the central axis TCL side end of lower protrusion pieces 722F to central axis TCL is smaller than the outer diameter of float F, float F does not move to the lower side than the top surface of lower protrusion pieces 722F.

As described above, according to the present embodiment, float F is disposed inside detecting reservoir 72R where the decontamination liquid is stored, and the fact that the liquid level of the decontamination liquid in liquid supplying reservoir 71R has reached the predetermined position is detected by using float F. In this manner, the liquid level position of the decontamination liquid in atomization device 100, which is the decontamination device used for the decontamination of culture device 1, can be correctly detected.

In addition, liquid level detection device 7 of the present embodiment does not require a special light-emitting sensor, and therefore can be manufactured at lower cost.

By setting the predetermined position to a position higher than the through hole of diaphragm 60 of atomization device 100, the vibration of diaphragm 60 can be stopped, with the lower half of the inner surface of at least the center portion of diaphragm 60 immersed in the decontamination liquid. In this manner, it is possible to prevent damage to diaphragm 60 due to the vibration with the region smaller than half the inner surface of the center portion of diaphragm 60 immersed in the decontamination liquid, or with the entire diaphragm 60 not immersed in the decontamination liquid. Note that it suffices that the predetermined position is set to the position on the upper side than the center of diaphragm 60 in the vertical direction.

The outer diameter of float F is sufficiently smaller than the inner diameter of upper cylindrical part 721. In this manner, the decontamination liquid does not form an annular bridge at a location between float F and upper cylindrical part 721 and a location higher than the liquid level of the decontamination liquid in the vertical direction. That is, float F does not adhere to the inner surface of upper cylindrical part 721 on the upper side than the liquid level. In this manner, float Fis smoothly lowered in upper cylindrical part 721 as the liquid level is lowered. Thus, liquid level detection device 7 can reliably detect the liquid level position of the decontamination liquid in liquid supplying reservoir 71R.

In addition, since the inner diameter of lower cylindrical part 722 is smaller than the inner diameter of upper cylindrical part 721, the amount of decontamination liquid remaining inside liquid level detection device 7 when the decontamination operation is completed can be reduced. Since the decontamination liquid remaining inside liquid level detection device 7 is discarded, the discarded decontamination liquid can be reduced by using liquid level detection device 7 of the present embodiment as atomization device 100. Thus, a decontamination operation using a smaller amount of decontamination liquid can be performed.

Further, since the outer diameter of lower cylindrical part 722 is smaller than the outer diameter of upper cylindrical part 721, a space for disposing sensor Se can be ensured at lower cylindrical part 722 disposed below upper cylindrical part 721.

Detecting reservoir 72R includes tapered cylindrical part 723 connected to upper cylindrical part and lower cylindrical part 722 whose inner diameter is smaller than upper cylindrical part 721, and the inner diameter of tapered cylindrical part 723 decreases as the distance to lower cylindrical part 722 decreases. Thus, float F is smoothly guided to detection space SP without interfering with the downward movement of float F at the boundary between upper cylindrical part 721 and lower cylindrical part 722. Thus, the liquid level of the decontamination liquid in liquid supplying reservoir 71R can be reliably detected.

Upper protrusion pieces 721F are formed in the inner peripheral surface of upper cylindrical part 721, and twice the distance from the central axis TCL side end of upper protrusion pieces 721F to central axis TCL is smaller than the outer diameter of float F, and thus float F does not fit to a portion between upper protrusion pieces 721F. In addition, the width size of the bottom surface of upper protrusion pieces 721F is small, and therefore, when liquid level detection device 7 is temporarily disposed upside down to discard the decontamination liquid remaining in liquid level detection device 7 as illustrated in FIG. 6, the amount of decontamination liquid that can remain between the outer peripheral surface of float F and the bottom surface of upper protrusion pieces 721F is small. In this manner, since float F less adheres to the inner peripheral surface of upper cylindrical part 721 and the bottom surface of upper protrusion pieces 721F, float F is not held at the upper part of detecting reservoir 72R when the orientation of liquid level detection device 7 is reset to the original orientation after the discard of the decontamination liquid.

In this manner, float F is lowered to detection space SP when the orientation of liquid level detection device 7 is reset to the original orientation after the decontamination liquid is discarded with temporarily liquid level detection device 7 disposed upside down for the discard of the decontamination liquid remaining in liquid level detection device 7. Thus, it is possible to prevent a situation where the liquid level position of the decontamination liquid is mistakenly detected as being higher than the predetermined position even when the decontamination liquid is not stored in liquid level detection device 7. In this manner, it is possible to prevent damage to diaphragm 60 due to the vibration of diaphragm 60 that is not immersed in the decontamination liquid at all.

A plurality of lower protrusion pieces 722F protruding toward central axis TCL of detecting reservoir 72R is formed at the inner peripheral surface of lower cylindrical part 722, and float F is in contact with the top surface of each of lower protrusion pieces 722F when float F is located on the lowermost side (see FIG. 7). In this manner, float F does not fit to the upper end of the tube (i.e., connection tube CT) connected with lower cylindrical part 722 and having an inner diameter smaller than lower cylindrical part 722. In addition, since a gap is formed between the plurality of lower protrusion pieces 722F, the air flows to liquid supplying reservoir 71R from the gap between air lower protrusion pieces 722F through connection tube CT even with float F in contact with each of lower protrusion pieces 722F when the decontamination liquid remaining inside liquid level detection device 7 is discarded. In this manner, the decontamination liquid can be discarded without leaving it in connection tube CT or inside detecting reservoir 72R.

Modification

It suffices that upper protrusion pieces 721F limits the upward movement of float F, and that at least a part of upper protrusion pieces 721F is located inside detecting reservoir 72R. Note that desirably, upper protrusion piece 721F has a shape with a smaller contact area with float F. In this manner, upper protrusion pieces 721F may not protrude toward central axis TCL of detecting reservoir 72R, and any number of upper protrusion pieces 721F may be provided. In addition, upper protrusion pieces 721F may not be formed inside detecting reservoir 72R.

For example, each of upper protrusion pieces 721F may have a straight and round rod shape. One end and the other end of each of upper protrusion pieces 721F may be connected to the inner peripheral surface of upper cylindrical part 721 so that it does not pass through central axis TCL of detecting reservoir 72R. In addition, one end of each of upper protrusion pieces 721F may be connected at a predetermined position outside detecting reservoir 72R, and the other end of each of upper protrusion pieces 721F may extend toward central axis TCL of detecting reservoir 72R inside detecting reservoir 72R.

It suffices that each of lower protrusion pieces 722F limits the downward movement of float F, and that each of lower protrusion pieces 722F is formed at the inner peripheral surface of lower cylindrical part 722. Note that desirably, each of lower protrusion pieces 722F has a shape with a smaller contact area with float F. In this manner, lower protrusion pieces 722F may not protrude toward central axis TCL of detecting reservoir 72R, and any number of lower protrusion pieces 722F may be provided.

For example, each of lower protrusion pieces 722F may have a straight and round rod shape. One end and the other end of each of lower protrusion pieces 722F may be connected to the inner peripheral surface of lower cylindrical part 722 so that it does not pass through central axis TCL of detecting reservoir 72R.

In addition, while liquid reservoir 7R is separated into liquid supplying reservoir 71R and detecting reservoir 72R in the above-described embodiment, liquid reservoir 7R may include only one reservoir, and the reservoir may have the functions of liquid supplying reservoir 71R and detecting reservoir 72R. In this case, liquid level detection device 7 does not include connection tube CT.

While liquid level detection device 7 of the above-described embodiment detects whether the liquid level of the decontamination liquid has reached a predetermined position by using float F, the liquid level position of the decontamination liquid may be detected at all times.

INDUSTRIAL APPLICABILITY

The liquid level detection device according to the present disclosure is applicable to atomization devices used for decontamination operations of culture devices. Therefore, its industrial applicability is wide.

REFERENCE SIGNS LIST

1 Culture device
R Culture chamber
2 Main body part
21 Depression
OH Outlet
3 Lid
4 Supporting member
5 Leg
51 Front leg
52 Rear leg
6 Atomization mechanism
60 Diaphragm
61 Holding member
62 Inner holding member
62R Supply path
63 Outer holding member 63R Jetting path
64 Nozzle
64H Jetting hole
SR Storage space
7 Liquid level detection device
7R Liquid reservoir
71R Liquid supplying reservoir
LS Liquid level
72R Detecting reservoir
SS Liquid level
721 Upper cylindrical part
721A upper portion
721B Lower portion
721C Connecting portion
721F Upper protrusion piece
722 Lower cylindrical part
722F Lower protrusion piece
723 Tapered cylindrical part
CT Connection tube
100 Atomization device
TCL Central axis
SSL Sensor detection line
F Float
Se Sensor
Sea Light emission part
Seb Light reception part
SP Detection space

The invention claimed is:

1. A liquid level detection device comprising:
a liquid reservoir configured to store hydrogen peroxide solution to be atomized by a diaphragm having a through hole;
a float disposed in the liquid reservoir; and
a sensor configured to detect a fact that a liquid level of the hydrogen peroxide solution stored in the liquid reservoir has reached a predetermined position, by using the float, wherein:
the liquid reservoir includes a detecting reservoir and a liquid supplying reservoir connected to the detecting reservoir by a connection tube at a position lower than the predetermined position in a vertical direction,
the connection tube is connected to a bottom of the detecting reservoir and a bottom of the detecting reservoir, and
the float is disposed in the detecting reservoir.

2. The liquid level detection device according to claim 1, wherein the predetermined position is located at a position higher than a center of the diaphragm in the vertical direction.

3. The liquid level detection device according to claim 1, wherein the detecting reservoir includes an upper cylindrical part and a lower cylindrical part located at a position lower than the upper cylindrical part in the vertical direction, and
wherein an inner diameter of the lower cylindrical part is smaller than an inner diameter of the upper cylindrical part and greater than an outer diameter of the float.

4. The liquid level detection device according to claim 3, wherein the detecting reservoir includes a tapered cylindrical part whose inner diameter decreases as a distance to the lower cylindrical part decreases, and
wherein the tapered cylindrical part is connected to the upper cylindrical part and the lower cylindrical part.

5. The liquid level detection device according to claim 3, wherein the sensor is located at a position lower than the upper cylindrical part in the vertical direction.

6. The liquid level detection device according to claim 1, wherein an upper protrusion piece configured to limit an upward movement of the float is formed, and
wherein at least a part of the upper protrusion piece is located inside the detecting reservoir.

7. The liquid level detection device according to claim 1, wherein a lower protrusion piece configured to limit a downward movement of the float is formed at an inner peripheral surface of the detecting reservoir.

8. An atomization device comprising:
the liquid level detection device according to claim 1; and
the diaphragm.

9. A culture device comprising the atomization device according to claim 8.

10. An atomization device comprising:
a liquid level detection device; and
a diaphragm, wherein:
the liquid level detection device comprises:
a liquid reservoir configured to store hydrogen peroxide solution to be atomized by the diaphragm having a through hole;
a float disposed in the liquid reservoir; and
a sensor configured to detect a fact that a liquid level of the hydrogen peroxide solution stored in the liquid reservoir has reached a predetermined position, by using the float, and
a center axis of the diaphragm crosses a vertical direction.

11. The atomization device according to claim 10, wherein the predetermined position is located at a position higher than a center of the diaphragm in the vertical direction.

12. The atomization device according to claim 10, wherein:
the liquid reservoir includes a detecting reservoir and a liquid supplying reservoir connected to the detecting reservoir at a position lower than the predetermined position in the vertical direction,
the float is disposed in the detecting reservoir, and
the diaphragm is disposed at the liquid supplying reservoir.

13. The atomization device according to claim 12, wherein:
the detecting reservoir includes an upper cylindrical part and a lower cylindrical part located at a position lower than the upper cylindrical part in the vertical direction, and
an inner diameter of the lower cylindrical part is smaller than an inner diameter of the upper cylindrical part and greater than an outer diameter of the float.

14. The atomization device according to claim 13, wherein:
the detecting reservoir includes a tapered cylindrical part whose inner diameter decreases as a distance to the lower cylindrical part decreases, and
the tapered cylindrical part is connected to the upper cylindrical part and the lower cylindrical part.

15. The atomization device according to claim 13, wherein the sensor is located at a position lower than the upper cylindrical part in the vertical direction.

16. The atomization device according to claim 12, wherein:
an upper protrusion piece configured to limit an upward movement of the float is formed, and
at least a part of the upper protrusion piece is located inside the detecting reservoir.

17. The atomization device according to claim 12, wherein a lower protrusion piece configured to limit a downward movement of the float is formed at an inner peripheral surface of the detecting reservoir.

* * * * *